(12) United States Patent
Kalvøy et al.

(10) Patent No.: US 10,716,489 B2
(45) Date of Patent: Jul. 21, 2020

(54) DETERMINING BIOLOGICAL TISSUE TYPE

(71) Applicant: OSLO UNIVERSITETSSYKEHUS HF, Oslo (NO)

(72) Inventors: Håvard Kalvøy, Vestby (NO); Axel Sauter, Oslo (NO); Audun Stubhaug, Oslo (NO); Sverre Grimnes, Oslo (NO); Ørjan G. Martinsen, Stabekk (NO)

(73) Assignee: Oslo Universitetssykehus HF, Oslo (NO)

( * ) Notice: Subject to any disclaimer, the term of this patent is extended or adjusted under 35 U.S.C. 154(b) by 505 days.

(21) Appl. No.: 15/518,034

(22) PCT Filed: Oct. 12, 2015

(86) PCT No.: PCT/EP2015/073597
§ 371 (c)(1),
(2) Date: Apr. 10, 2017

(87) PCT Pub. No.: WO2016/055666
PCT Pub. Date: Apr. 14, 2016

(65) Prior Publication Data
US 2017/0296090 A1    Oct. 19, 2017

(30) Foreign Application Priority Data
Oct. 10, 2014    (GB) .................................. 1417963.4

(51) Int. Cl.
*A61B 5/053*    (2006.01)
*A61B 5/00*    (2006.01)
*A61B 5/06*    (2006.01)

(52) U.S. Cl.
CPC ............ *A61B 5/053* (2013.01); *A61B 5/0537* (2013.01); *A61B 5/0538* (2013.01); *A61B 5/068* (2013.01); *A61B 5/4893* (2013.01); *A61B 5/7264* (2013.01)

(58) Field of Classification Search
CPC ..... A61B 5/053; A61B 5/0537; A61B 5/0538; A61B 5/068; A61B 5/4893; A61B 5/7264
See application file for complete search history.

(56) References Cited

U.S. PATENT DOCUMENTS

| | | | |
|---|---|---|---|
| 6,723,049 B2 * | 4/2004 | Skladnev | ............... A61B 5/053 600/372 |
| 8,290,578 B2 * | 10/2012 | Schneider | .............. A61B 5/053 600/547 |
| 2012/0226272 A1 * | 9/2012 | Chernov | ............... A61B 5/0295 606/34 |

FOREIGN PATENT DOCUMENTS

| | | |
|---|---|---|
| EP | 1266612 A2 | 12/2002 |
| WO | 2010105261 A2 | 9/2010 |

OTHER PUBLICATIONS

Kalvoy, "Determination of Tissue Type Surrounding a Needle Tip by Electrical Bioimpedance", Engineering in Medicine and Biology Society, 2008. EMBS 2008. 30th Annual International Conference of the IEEE, IEEE, Piscataway, NJ, Aug. 20, 2008, pp. 2285-2286.

(Continued)

*Primary Examiner* — Devin B Henson
(74) *Attorney, Agent, or Firm* — Eversheds Sutherland (US) LLP (57) ABSTRACT

A method is described for determining biological tissue type based on a complex impedance spectra obtained from a probe with a conducting part adjacent a tissue region of interest, wherein the impedance spectra includes data from a number of frequencies. The method may include: obtaining, from the complex impedance spectra, a first data set (Continued)

representative of impedance modulus values, or equivalent admittance values, at one or more frequencies, obtaining, from the complex impedance spectra, a second data set representative of impedance phase angle values, or equivalent admittance values, at one or more different frequencies, applying a first discrimination criterion to the first data set, applying a second discrimination criterion to the second data set, and thereby determining if the tissue region of interest is a tissue type characterised by the discrimination criteria.

16 Claims, 4 Drawing Sheets

(56) References Cited

OTHER PUBLICATIONS

Office Action, JP2017-519267, dated Oct. 24, 2019 (in Japanese) (7 pp.).
Office Action, JP2017-519267, dated Oct. 24, 2019 (in English) (8 pp.).

* cited by examiner

DETERMINING BIOLOGICAL TISSUE TYPE

TECHNICAL FIELD

The present invention relates to determining biological tissue types. In particular, the invention relates to methods and apparatuses for determining biological tissue types by measuring electrical impedance values of the biological tissue. One example involves discrimination of intraneural nerve tissue from other tissue types such as muscle tissue, fat, connective tissue and intravascular tissue.

BACKGROUND OF THE INVENTION

It is often of interest to be able to determine the type of biological tissue that was surrounding a probe inserted into the human or animal body at locations or under circumstances that do not allow for inspection by other means. When administering drugs, tracers or taking biopsies, it is often critical to position the tip of a needle at a specific position or in a specific tissue type. Serious implications and undesired results may incur if the needle unintentionally hits or penetrates veins, arteries, lungs or nerves. In regional anaesthesia, such as peripheral nerve blocks, drugs must be injected close to a nerve. Wrong or imprecise injection of the anaesthesia results in little or no effect. Injections within the nerve, on the other hand, can give nerve damage that can lead to persistent motor or sensory impairment and debilitating neuropathic pain. Biopsies are carried out by insertion of a needle that can cut and extract a small tissue sample. It may, however, be difficult to ensure that the extracted sample is of the desired tissue type without some form of guidance.

To avoid potential complications, some sort of guidance is used in critical cases. High risk procedures are often carried out under guidance of advanced apparatuses such as X-ray, CT, ultrasound, or MR imaging. Ultrasound images reveal abrupt changes in acoustical impedance, but are insensitive to homogeneous regions. X-ray images have poor contrast in soft tissues. MRI is sensitive to soft tissue properties, but is complicated to use and requires MRI compatible needles and moving of the patient to a MRI clinic. It is a common disadvantage of the use of these types of guiding techniques that the required equipment is complicated and expensive in relation to the frequent and relatively simple task of inserting a needle with reasonable precision.

US 2003/109871 describes an apparatus for detecting and treating tumours using localized impedance measurement. The impedance measurement configuration is described in paragraph [0060] in relation to FIG. 3A. From here it appears that members 22m define sample volumes by means of conductive pathways (22cp) to either between each other or to a common ground electrode (22g or 22gp). It thus appears that the apparatus always measure the impedance of a sample volume of interest (5sv). By switching the electrodes between which the measurement is made, the conductive pathway 22cp is changed which again alters the shape and size of the associated sample volume. It is a disadvantage of the apparatus described in US 2003/109871 that it measures impedance in relatively large volumes.

WO 2007/075091, which describes earlier work forming a starting point for the work of the current inventors, describes the use of a probe such as a needle to determine data that relates to tissue type. As described in this document, a probe can be used to obtain an electrical impedance spectrum relating to the tissue adjacent a specified location on the probe, typically a tip of a needle. It would be highly beneficial for the user to be able to determine the type of tissue from the impedance spectrum. This would mean that the tissue type can be determined without the need for further invasive or non-invasive procedures. However, WO 2007/075091 provides no teaching regarding general techniques for determining specific tissue types, and in fact only describes the possibility of a comparison with earlier impedance spectra with newly measured impedance spectra, thereby making a suggestion of a tissue type match when the newly measured spectra is similar to an earlier measured spectra with known tissue type. This process is limited in its accuracy and utility. The impedance spectra can vary not only with tissue type, but also with physiological conditions. The impedance spectra from different patients or using different measurement set-ups will vary. Thus an exact match may not be possible and even if achieved it may not be accurate. What is needed therefore is a more accurate and more generally applicable way to use the impedance spectra to determine tissue type.

SUMMARY OF THE INVENTION

Viewed from a first aspect the invention provides a method of determining biological tissue type based on a complex impedance spectra obtained from a probe with a conducting part adjacent a tissue region of interest, wherein the impedance spectra includes data from a plurality of frequencies the method comprising: obtaining, from the complex impedance spectra, a first data set representative of impedance modulus values, or equivalent admittance values, at one or more frequencies; obtaining, from the complex impedance spectra, a second data set representative of impedance phase angle values, or equivalent admittance values, at one or more different frequencies; applying a first discrimination criterion to the first data set; applying a second discrimination criterion to the second data set; and thereby determining if the tissue region of interest is a tissue type characterised by the discrimination criteria.

The method allows for tissue type to be determined based on a much simpler and more reliable technique than that proposed by WO 2007/075091. Moreover, the same basic input data is required, and the new method of the first aspect is far less sensitive to variations in the measuring equipment.

There may optionally be further discrimination criteria. For example two discrimination criteria may be applied to the second data set. The discrimination criteria may comprise threshold values for characteristics of the data set at given frequencies. For example, the first discrimination criterion may comprise determining if the impedance modulus is above or below a threshold impedance value at a set frequency. The second discrimination criterion may comprise determining if the value of the phase angle is above or below a threshold value at a given frequency. Alternatively, or as an additional discriminator, the second discrimination criterion may comprise determining if the gradient of the phase angle, as it changes with frequency, is above or below a threshold value at a given frequency. The frequencies for the various discrimination criteria used to identify the tissue type will generally be different frequencies. As referenced above, the impedance modulus and phase angle should also be taken to encompass equivalent transformed values, for example admittance values.

The method preferably includes defining the discrimination criteria by identifying frequencies at which appreciable differences in either impedance or phase angle exist for different tissue types, for example by finding frequencies where the differences peak, and by setting threshold values that separate different tissue types from one another. Impedance values are sensitive to the measured volume and the cross-section that the current must pass through. Consequently it can be useful to determine suitable values by reference to earlier measurements using the same or similar measurement equipment as will be used for later identification of the tissue type.

As will be understood, alternative sets of discrimination criteria of the same type could be used for identifying other tissue types. It will be seen from the examples presented herein that, by the use of both modulus data and phase angle data, patterns can be identified that permit the identification of specific tissue types using a relatively small number of discrimination criteria at carefully selected frequencies. The method may include comparison of impedance spectra for known tissue types in order to identify frequencies at which data parameters such as impedance modulus, phase angle, and phase angle gradient have the greatest difference for different tissue types, and selecting discrimination criterion at these frequencies to thereby provide a method for identifying a desired tissue type. The method may include the use of a compound variable determined based on weighted and/or normalised values for two or more of impedance modulus, phase angle, and phase angle gradient, preferably using all three of impedance modulus, phase angle, and phase angle gradient. In one example the compound variable includes one term based on a multiple of the impedance modulus at a first frequency, optionally with an adjustment in magnitude, with the phase angle at a second frequency, optionally with an adjustment in magnitude, and a second term based on the phase angle gradient. The first frequency and the second frequency may be the same, although in some cases it will be found that better discrimination can be achieved with differing frequencies used for the impedance and phase angle measurements.

The method may be for determining if the tissue region of interest is nerve tissue such as the epineurium, the perineurium, or the nerve fibres themselves. It is important in many cases to detect either contact with the nerve fibres or contact with the tissue immediately adjacent the nerve fibres. If direct contact with the nerve is detected then the instrument should often be removed to avoid damage. If proximity to the nerve fibres is detected via contact with the epineurium or perineurium then the user may know to avoid further advancing of the instrument. Hence, the discrimination criteria may be defined by identifying frequencies at which appreciable differences in either impedance or phase angle exist for these types of nerve tissue compared to other tissue types such as subcutaneous fat and muscle as well as different types of nerve tissue.

In one example, the first discrimination criterion is whether or not the impedance modulus is below a value known to exclude subcutaneous fat tissue, which generally has higher impedance than perineural tissue and intraneural tissue. The threshold value may be a maximum boundary on impedance within a given frequency range for the impedance measurements, such as a value of 2500 Ohms, optionally 2200 Ohms, within a frequency selected from the range 10 kHz to 50 kHz, or at least above 10 KHz, optionally in the range 25 kHz to 45 kHz. This will exclude subcutaneous fat tissue. For example, the criterion may require an impedance of less than 2200 Ohms at a frequency of about 39 kHz.

For determining direct contact with nerve tissue such as the nerve fibres, a second discrimination criterion applied to the phase angle may be to determine if the phase angle at a set frequency is above a threshold level that is known to exclude other tissue types, such as muscle and perineural nerve tissue. The threshold level may for example require a phase angle of less than 30 degrees, optionally less than 25 degrees, for a frequency selected from the range 10 kHz to 50 kHz, optionally in the range 25 kHz to 45 kHz. This will exclude muscle tissue and perineural tissue, or if used in the opposite sense, i.e. requiring a minimum phase angle of 30 degrees in the given frequency, then it would exclude intraneural tissue and subcutaneous fat. In one. example for identifying intraneural tissue the criterion may require a phase angle of less than 25 degrees at about 39 kHz.

Advantageously, some example embodiments require a maximum impedance threshold value and a maximum phase angle threshold level that is measured at the same frequency. This can minimise the range of frequencies required for the impedance measurements.

An alternative second discrimination criterion, which could optionally be a third discrimination criterion used together with the second discrimination criterion described above, may be to determine if the gradient of the phase angle at a set frequency is above a threshold level or within a range that includes a nerve tissue type of interest but is known to exclude other tissue types, such as muscle and other nerve tissue types.

In some cases, where it is of interest to identify intraneural tissue then this criterion may require a phase angle gradient producing an increase in phase of at least 3 degrees between 125 kHz and 251 kHz, i.e. a gradient of at least $3/126$ or 0.0238 degrees per kHz, preferably a gradient of at least 0.06 degrees per kHz, optionally at least 0.09 degrees per kHz at frequencies above 10 kHz, more preferably at frequencies above 100 kHz and optionally at frequencies below 400 kHz, preferably below 300 kHz. Muscle and perineural nerve tissue have lesser gradients at these frequencies and thus this criterion can distinguish intraneural tissue from muscle and perineural nerve tissue. In one example, the criterion may require an increase of larger than 3 degrees for the phase angle at 251 kHz compared to the phase angle at 125 kHz. In another example the criterion may require a minimum change in phase angle, based on a gradient value as set out above, for measurements at 126 kHz and 158 kHz.

In another example, where it is of interest to identify perineural tissue then the method may include determining if the phase angle gradient is within a threshold range at a given frequency, for example a frequency above 100 kHz with an upper value on gradient set to exclude intraneural tissue and subcutaneous fat, and a lower value on gradient set to exclude muscle. At these frequencies it is found that perineural tissue as an intermediate gradient compared to the other tissues, with often the intraneural tissue and subcutaneous fat often having a large positive gradient in phase angle, and the muscle having a negative gradient in phase angle. The threshold range may exclude negative phase angle gradients and phase angle gradients above 0.06 degrees per kHz, optionally above 0.03 degrees per kHz.

It will be appreciated that the use of the first criterion with one of the second and third criteria, with one applied to modulus data and one to phase angle data at values within the ranges discussed above, or at the specific example values, will permit tissues such as nerve fibre tissue, or other nerve tissues to be discriminated from various other tissue types including subcutaneous fat, and muscle as well as other nerve tissue types not of interest, i.e. perineural and epineural tissue in the case where the tissue of interest is nerve fibres. To ensure increased accuracy, it is preferred for both of the second and third discrimination criteria to be used together, in particular when discriminating intraneural tissue.

The method of the first aspect may use pre-recorded impedance spectra. That is to say, in preferred embodiments the method is purely a method of processing of the impedance spectra data and does not include gathering of the data. Thus, in preferred embodiments the method may be defined as a non-surgical data processing method without any surgical steps and in particular without including the step of inserting the probe within the body to obtain the impedance spectra.

Alternatively, the method may include recording a suitable impedance spectrum and hence may involve the use of an appropriate probe inserted into the human or animal body to record complex impedance data.

Preferably, the impedance spectrum is provided in electronic form. Thus, the method may use a computer or similar data processing apparatus for processing the impedance spectra data.

Viewed from a second aspect, the invention provides a computer programme product comprising instructions that, when executed, will configure a data processing apparatus to carry out the method of the first aspect and optionally of some or all of the preferred and/or optional features described above.

In a third aspect, the invention provides an apparatus for determining biological tissue type based on a complex impedance spectra obtained from a probe with a conducting part adjacent a tissue region of interest, wherein the impedance spectra includes data from a plurality of frequencies the apparatus comprising a processor arranged to: obtain, from the complex impedance spectra, a first data set representative of impedance modulus values, or equivalent admittance values, at one or more frequencies; obtain, from the complex impedance spectra, a second data set representative of impedance phase angle values, or equivalent admittance values, at one or more different frequencies; apply a first discrimination criterion to the first data set; apply a second discrimination criterion to the second data set; and to thereby determine if the tissue region of interest is a tissue type characterised by the discrimination criteria.

The processor may optionally be arranged to carry out some or all of the preferred and/or optional steps discussed above in relation to the first aspect.

The apparatus may be supplied with a pre-recorded impedance spectra. Alternatively, the apparatus may include a device for recording a complex impedance spectra, for example a device as described in WO 2007/075091.

These and other features and improvements of the present application and the resultant patent will become apparent to one of ordinary skill in the art upon review of the following detailed description when taken in conjunction with the several drawings and the appended claims.

BRIEF DESCRIPTION OF THE DRAWINGS

Certain preferred embodiments of the invention will now be described by way of example only and with reference to the accompanying drawings in which.

DETAILED DESCRIPTION

The currently proposed method and apparatus uses impedance spectra to identify the tissue type. This is based on precise determinations of local impedance values in biological tissue surrounding a tip of a probe such as a needle. Such impedance values allow localized determination of the tissue type and thereby determination of an anatomical positioning of the probe. This then allows for adjustments to the positioning of the probe.

The measurement of impedance spectra for use as input data for the method and apparatus proposed herein can be achieved in any suitable way. What is important is that the impedance of the tissue can be measured with an electrical signal applied via the probe over a range of frequencies, and that the measured/recorded spectra is a measured AC-impedance of the type that can be expressed as a complex number and split in a real part named resistance (R) and an imaginary part named reactance (X). By mathematical transformation the same impedance can be expressed as an impedance modulus ($|Z|$) and phase angle ($\varphi$). In similar way the measured value can be expressed as an admittance with a real part (conductance, G) and imaginary part (susceptance, B), or an admittance modulus ($|Y|$) and phase angle ($\varphi$). It will of course be understood that no matter what transformation or notation is applied, the underlying data would be the same.

One example apparatus for the measurement and recording of impedance spectra is similar to that proposed in WO 2007/075091. The apparatus is improved, as proposed herein, by the additional functionality required to correctly determine tissue type without the need for comparison with earlier measured spectra. Thus, the measurement apparatus may comprise:

an electronic processing unit with an impedance measuring circuit for registering an impedance signal;

a monopolar impedance measuring setup comprising a probe having an electrically conducting part to be inserted into a subject and a current-carrying electrode to be positioned on the skin of the subject, the conducting part of the probe and the current-carrying electrode being in electrical connection with the impedance measuring circuit;

the impedance measuring circuit comprising an alternating current or voltage source connected to provide an alternating current or voltage driving signal to the conducting part of the probe and to the current-carrying electrode;

the monopolar impedance measuring setup being configured to at least substantially eliminate impedance contributions from the current-carrying electrode; and the electronic processing unit being arranged to: vary a frequency of the driving signal from the source; calculate complex impedance values from the driving signal and the impedance signal for multiple frequencies of the driving signal to form a complex impedance spectrum; and to determine a tissue type surrounding the conducting part of the probe based on the complex impedance spectrum as discussed in further detail below.

In a refinement to this, the driving signal can also be a combination of more than one frequencies for simultaneous multi-frequency measurement making use of the principle of superposition. This will give the same results, but can be done more quickly and hence provides advantages when it is important to minimise the measurement time.

Since impedance values are determined using an AC driving signal, different driving signal frequencies yields different impedance values. Throughout the present description, spectral impedance values refer to impedance values at two or more different frequencies. The impedance vs. frequency spectrum $Z(f)$ characterizes the tissue to a much higher degree than single impedance values. The spectrum for different tissue types may be similar in some frequency intervals and very dissimilar in others. Also, impedances in some frequency intervals may be subject to large changes when the state of the tissue changes, while remaining almost unaffected in other frequency intervals. Thereby, the determination of tissue type may be based on one or several segments of the impedance spectrum. This is advantageous since it allows for a much more fine distinction between tissue types under changing conditions.

This example applies the electrical impedance (ratio of voltage to current) to characterise tissue. One skilled in the art will recognise that the admittance (ratio of current to voltage) may be applied equivalently. The reference herein to a signal indicative of impedance includes both impedance and admittance.

Alternative mechanisms may be used to ensure that the measured impedance is due to the tissue surrounding the conducting part of the probe. One possibility to ensure a measurement localized at the conducting part of the probe is to use an additional electrode, i.e. a reference electrode, on the skin of the patient and to configure the impedance measuring circuit to at least substantially eliminate impedance contributions from the reference electrode and the current-carrying electrode. In one example, an active operational amplifier circuit is applied, which comprises an operational amplifier having a first input connected to the signal source, a second input connected to the reference electrode and an output connected to the current-carrying electrode. In this monopolar electrode set-up, the current from the AC signal is drawn between the conducting part of the probe and the current-carrying electrode, whereas the impedance is measured between the conducting part of the probe and the reference electrode. Thereby, any error contribution from the tissue contacting reference electrode and the current-carrying electrode is eliminated—the measured impedance is due only to the tissue surrounding the conducting part of the probe.

In an alternative set-up, a measurement localized at the conducting part of the probe is ensured by using a current carrying electrode which is significantly larger than the area of the conducting part of the probe. The required ratio is dependent on the impedance of the skin, which itself may vary, and on the contact of the electrode material with the skin. In a preferred implementation the size of the current carrying electrode is at least 200 times larger, preferably at least 1000 times larger, than the conducting part of the probe. As discussed in WO 2007/075091, the impedance measuring circuit and setup may be configured so that only tissue within a given distance from the conducting part of the probe ('first surface part' in the prior art reference) contributes to the measured tissue impedance values. Hence, it may be preferred that the impedance measuring circuit and setup are configured so that the measured tissue impedance values are substantially determined by tissue within a given distance from the conducting part of the probe, the given distance being less than 10 mm, such as less than 8 mm, 5 mm, 3 mm, 2 mm, or 1 mm. By "substantially" is meant that the measured value may depend only very little on tissue not within the given distance, e.g. so that the variation of the measured value as a function of this distant tissue is smaller than the precision required to distinguish between tissue types. Thereby, an unambiguous determination of tissue type within the given distance may be made regardless of the tissue outside the given distance.

The measured impedance values depend on the characteristics of the conducting part of the probe—such as on area, shape, and surface properties, such as roughness, material conductivity etc. Therefore, the measured impedance values are to some degree characteristic for each probe or probe type. With the method of WO 2007/075091 this is a major problem since any change to the probe can stop the spectra matching process from working. This problem is greatly reduced with the currently proposed method and apparatus, which makes uses of known measurement devices in a new method and apparatus for determining different tissue types. The new method is based on the finding that by varying the measurement frequency in a specific range, and by considering certain defined criteria and threshold values, then tissues such as nerve tissue can be identified and discriminated from surrounding tissue types. The proposed method has been extensively tested using, as an example, the sciatic nerve in pigs.

The new developments involve the use of a defined frequency range to extract and assemble characteristic properties in a measured impedance spectra, or equivalent data set. The crucial step is not only to analyse the absolute values of the measurement, but also to use the pattern of the frequency response as a "fingerprint" to recognize the different tissue types. Unlike the method of WO 2007/075091 it is not necessary to make an exact match to earlier measurements. Instead, a set of simple criteria are generated, which have a wide applicability and can be used with measurements from any suitable system for gathering impedance spectra or the like from body tissues.

As noted above, a measured AC-impedance can be expressed as a complex number and split in a real part named resistance (R) and an imaginary part named reactance (X). By mathematical transformation the same impedance can be expressed as an impedance modulus ($|Z|$) and phase angle ($\varphi$). In similar way the measured value can be expressed as an admittance with a real part (conductance, G) and imaginary part (susceptance, B), or an admittance modulus ($|Y|$) and phase angle ($\varphi$).

The new ideas described herein use the patterns in a measured complex impedance spectrum, with the variations at different frequencies being used as an additional parameter to more common comparison of absolute impedance values. An example is explained below with reference to the Figures and the detection of nerve tissue. To the naked eye the nerve tissue specific pattern is most easily detected when the phase angle is plotted as a function of frequency as showed in FIGS. 2A-2D and FIG. 4, but in principle any measured impedance or admittance parameter can be mathematically derived from each other. Hence, the new concept is not only limited to the phase angle, but also includes the use of all other equivalent impedance and admittance parameters.

In the example impedance measurement series in pigs in-vivo a beta-dispersion was found when placing the needle tip in the sciatic nerve. This was in the beta-dispersion range at a characteristic frequency slightly higher than typical for muscle tissue. For the absolute values of the impedance modulus, resistance and reactance, no distinct differences could be found for nerve tissue compared to the measurements in other tissue types. However, when the phase angle is calculated as a function of frequency, then the plots showed patterns that were specific for nerve tissue in the frequency sweeps above 10 kHz. Based on analysis of the complete data set it was found that a pattern recognition of the phase angle as a function of measurement frequency could be used for the discrimination of the nerve tissue.

This process is not specific for a given measurement system. It can be used with any system able to perform multi frequency measurements with an electrode setup designed for very high sensitivity in the closest proximities to the probe/needle tip. The inventors have successfully used many different setups and needle types for this type of measurement.

The measurement series on pig models used monopolar measurements of complex impedance done with needle type 2 as described in "Impedance-based tissue discrimination for needle guidance" by Håvard Kalvøy et al, 2009 Physiol. Meas. 30 129, doi:10.1088/0967-3334/30/2/002. Raw data from ninety five measurements series in different tissue types done in eight pigs are included in FIGS. 1A-1D and FIGS. 2A-2D. Each of these measurement series contains twenty six measurements at different frequencies.

FIGS. 1A-1D show modulus plotted as function of frequency (1 kHz to 316 kHz) for ninety five measurement series with needle positions in Intraneural (A), Muscle (C), Perineural (B) and Subcutant fat (D). FIGS. 2A-2D show, for the same measurement series, the phase angle plotted as function of frequency (1 kHz to 316 kHz) from ninety five measurement series with needle positions in Intraneural (A), Muscle (C), Perineural (B) and Subcutant fat (D).

An intraneural nerve tissue specific beta-dispersion can be seen in the measurements. A simple way to describe such a frequency dependent tissue properties can be to calculate the change in phase angle (delta-φ) as a function of frequency for characteristic frequency range. Tissue discrimination can then be done by comparing in the tissue specific delta-φ in the measured data. For intraneural nerve tissue we found a characteristic increase in delta-φ starting at 20-30 kHz with a maximal delta-φ about 100-150 kHz. The delta-φ typical for muscle and perineural tissue started to increase at 5-10 kHz and had its max around 30 kHz. The according frequencies for subcutaneous fat were 30-50 kHz and about 150-200 kHz.

By recognizing these patterns we can discern the tissue types. To determine delta-φ we must measure with at least two different frequencies within the relevant range. However, increasing the range and number of frequencies will most probably make the discrimination more robust.

In subcutaneous fat we found the typical impedance modulus to be above 2200Ω for this needle set-up. This is higher than we found in the other tissue types and in good agreement with earlier studies. The measurements also showed a phase angle level above 25 degrees for muscle tissue between 15 kHz and 80 kHz. Solely level analysis has not yet been able to facilitate a commercial nerve detection method, but of course one should assume an enhanced quality of the method by including information found in the levels of other impedance and admittance parameters (modulus, resistance, susceptance, etc.).

Figure 1:
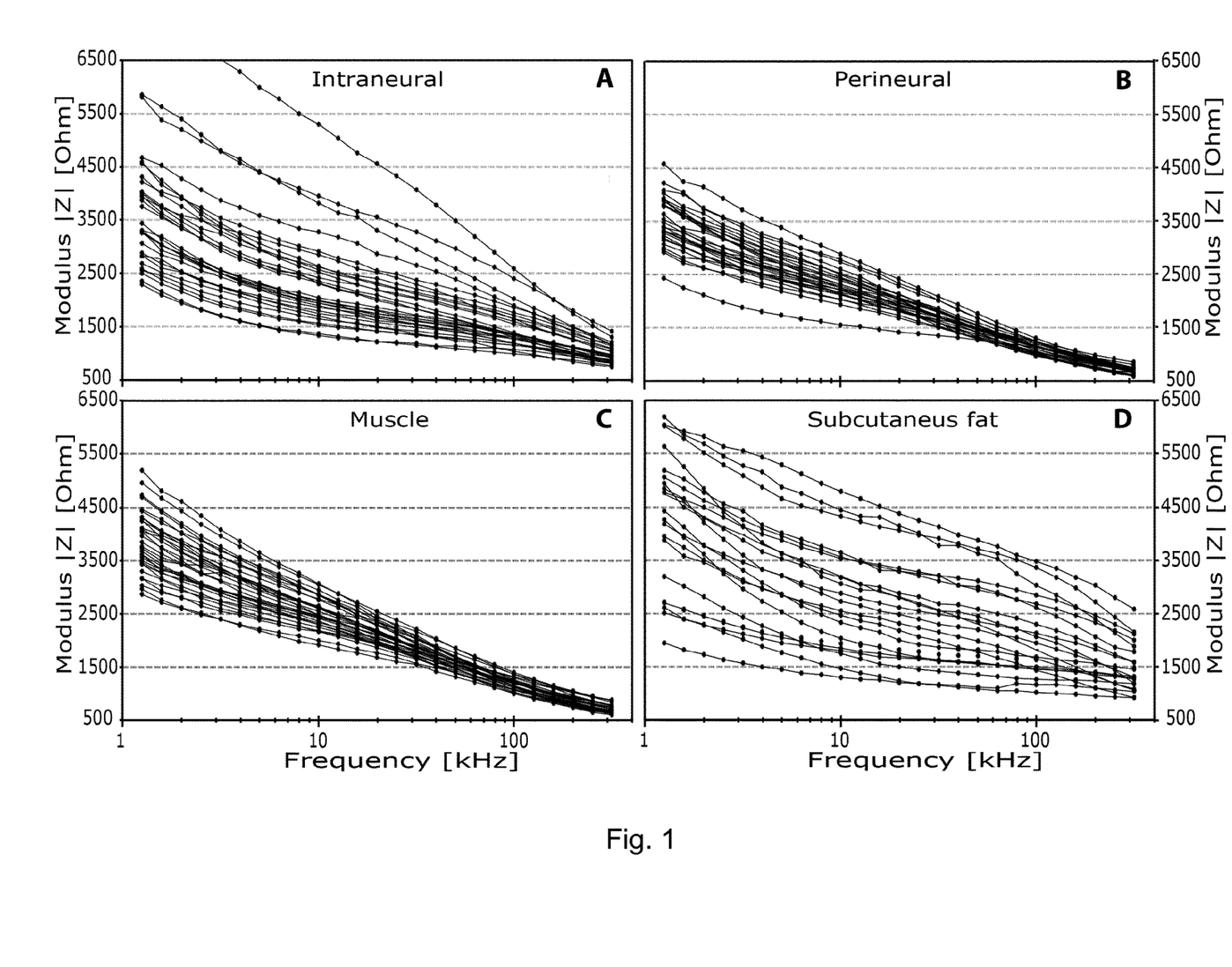
FIGS. 1A-1D are graphs showing modulus plotted as function of frequency (1 kHz to 316 kHz) for ninety five measurement series with needle positions in (A) intraneural tissue, (B) muscle tissue, (C) perineural tissue and (D) subcutaneous fat.
Figure 2:
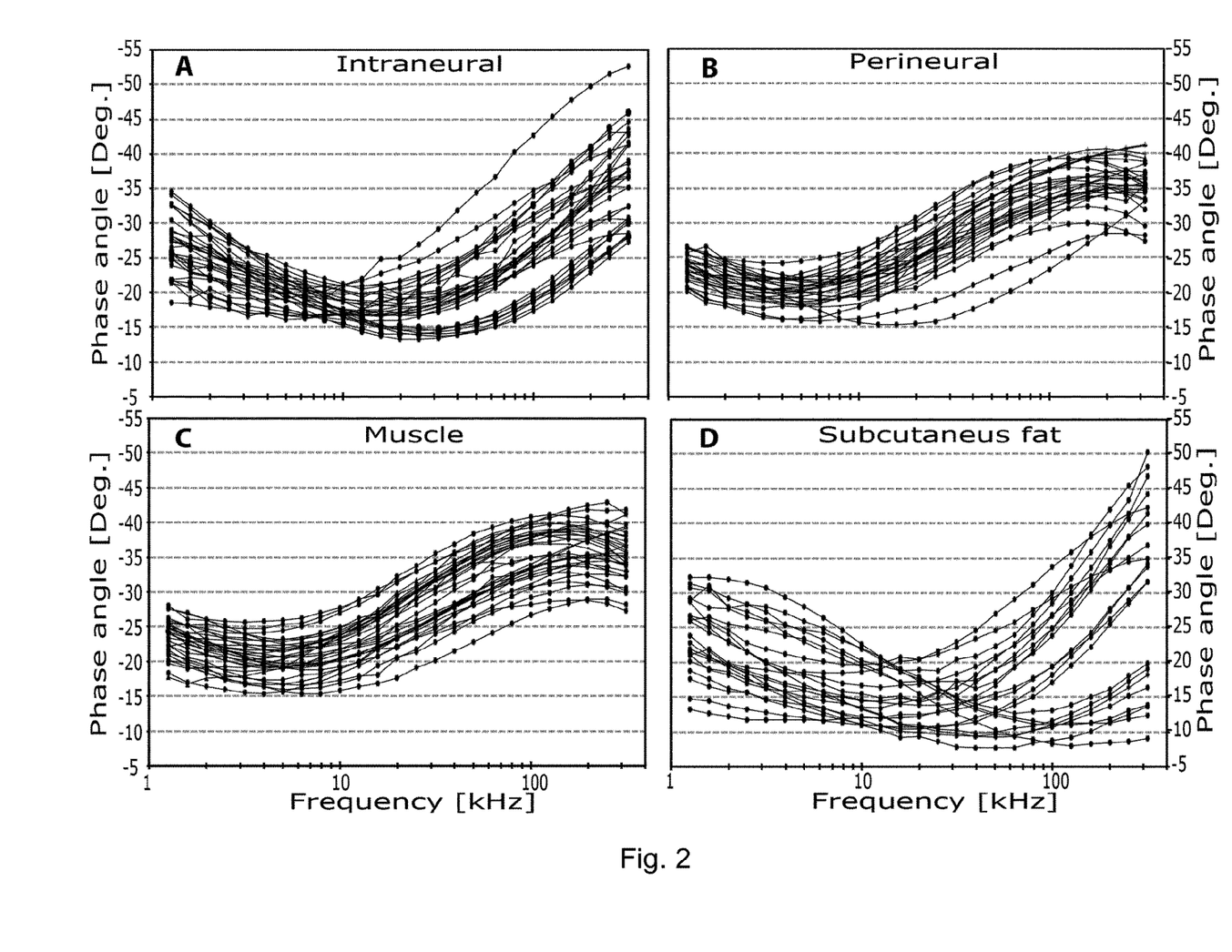
FIGS. 2A-2D are graphs showing phase angle plotted as function of frequency (1 kHz to 316 kHz) from ninety five measurement series with needle positions in (A) intraneural tissue, (B) muscle tissue, (C) perineural tissue and (D) subcutaneous fat.
Figure 3:
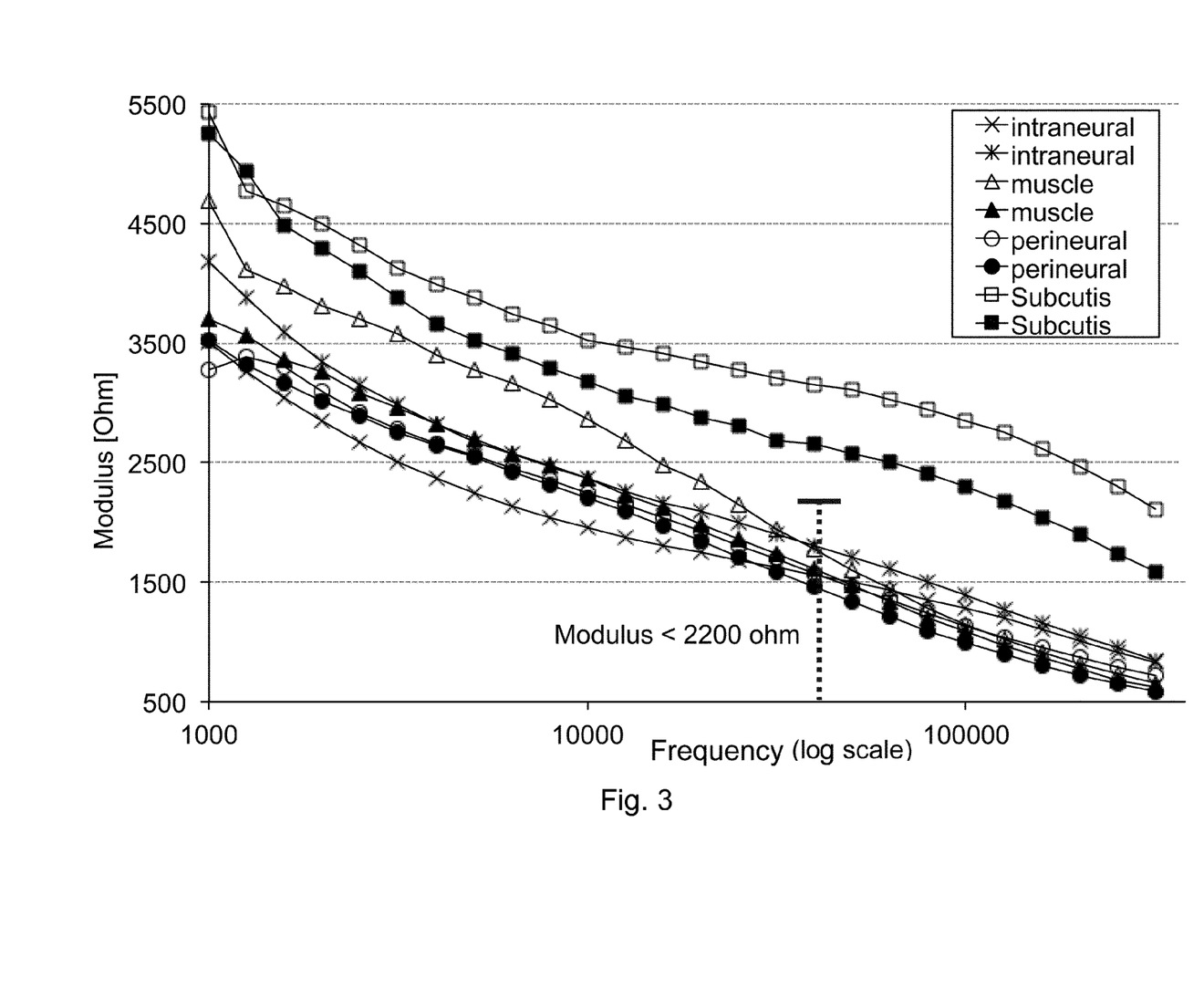
FIG. 3 shows modulus measurements for various tissue types and a proposed measurement criterion C1.
Figure 4:
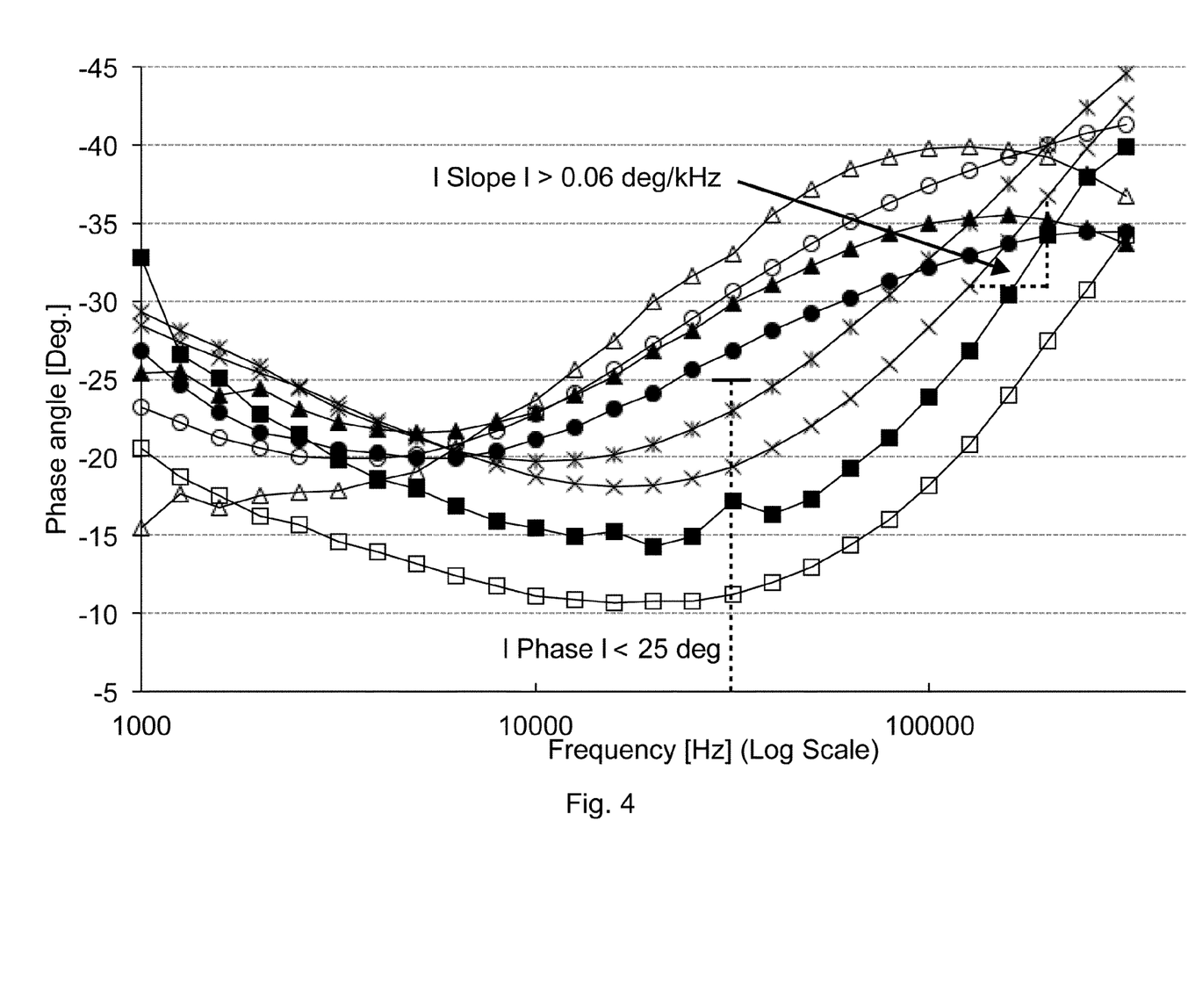
FIG. 4 shows phase angle measurements for various tissue types and two further proposed measurement criteria C2 and C3.

For an exemplary nerve detection algorithm we define three test criterions (C1, C2 and C3). To exclude the typical fat measurements we define C1 by setting 2200Ω as the upper limit for the impedance modulus at 39 kHz. The beta-dispersion related information in the phase angle was used in C2 by setting 3 degrees as the lower limit for delta-φ between 125 kHz and 251 kHz, and 25 degrees as the upper limit for the phase angle at 39 kHz in C3.

| | |
|---|---|
| C1: (Modulus level) | $\|Z(39\ kHz)\| < 2200\ \Omega$ |
| C2: (delta-φ) | $\|\varphi(251\ kHz)\| - \|\varphi(125\ kHz)\| > 3°$ |
| C3: (Phase angle level) | $\|\varphi(39\ kHz)\| < 25°$ |

Typical measurement data and a graphical illustration of these test criteria are shown in FIG. 3 and FIG. 4. Our experience is that these types of frequency analysis and pattern recognition are crucial for the development of a reliable nerve discrimination algorithm. It will be appreciated that in the example of FIG. 3 and FIG. 4, the threshold values could have been set higher or lower whilst achieving the same effect. Thus, for the impedance a threshold for C1 of anywhere between about 1800Ω and 2600Ω would differentiate between the tissue types, and for the phase angle a value for C3 of anywhere between 23° and 27° or a delta-φ for C2 of at least about 9° would differentiate between tissue types. Thus, for example, an alternative definition for C2 could be a requirement for at gradient of at least 0.06 degrees per kHz at some specified frequency around 125 kHz or within the range 126 kHz to 251 kHz. It will also be seen that the example thresholds would still operate effectively even if there were some shift along the frequency axis for phase angle, or some change in absolute values for impedance. Both of these changes can occur when different needle types are used. Hence, although the values proposed herein are based on measurements for one needle type they would nonetheless provide differentiation for different types of needles as well.

In a similar example using the same data, an algorithm for bioimpedance measurements to detect intraneural tissue, and discriminate it from surrounding tissue types, was developed by analysing the complex impedance dataset. Several impedance variables were combined in a compound variable C to optimise tissue discrimination. The compound variable used was:

$$C = \sqrt{\left(\frac{(-M_{126kHz} - 73.8) \times (P_{40kHz} - 65.9)}{562}\right)^2 + \left(\frac{(P_{158kHz} - P_{126kHz} + 2.27)}{0.95}\right)^2}$$

Where M is the impedance modulus at the specified frequency and P is the phase angle at the specified frequency. This compound variable thus uses both impedance modulus and phase angle, with adjusted values and a weighting, along with the phase angle gradient through use of a phase angle difference, again with an adjustment and a weighting. It will be appreciated that dependent on the particular needle arrangement and the tissue to be identified then a different set of frequencies and/or a different set of constants could be used in a similar compound variable to discriminate intraneural tissue or a differing tissue type.

The absolute values of modulus and phase angle are highly dependent on the measurement setup and the used electrodes, so the levels will have to be adjusted to match the type of hardware in use. The analyses of delta-φ is based on the tissue specific beta-dispersion witch is less influenced by the properties of the electrodes and measurement system. Hence, this type of frequency pattern recognition is less vulnerable to inconstancies in the measurement setup.

The new method and the simple algorithm described above were tested in a pig model with very good results in a prototype device.

In this example the nerve tissue (sciatic nerve) has a dispersion at a slightly higher frequency range than the beta-dispersion found in muscle tissue. This then allows for discrimination of the nerve tissue. Naturally, the muscle tissue could be identified using a similar method, which would be set up to exclude nerve tissue. Similar tissue properties can also be found by analysing the real and imaginary part of the impedance (R and X) or admittance (G and B).

The method is suited for use in combination with other methods for guiding, e.g. Ultrasound and/or Nerve-stimulator. Ultrasound can be used freely in parallel with the impedance measurements, since there is no interference between the two. For a combination with a nerve stimulator multiple frequency bio-impedance measurements can be made in the pauses between the stimulation pauses. For electrical nerve stimulation square pulses with a current between 0 mA to 5 mA are typically used. The impulse duration of these square pulses is typically 0.1 ms, applied with a frequency of 1 Hz. Hence during a one second stimulation cycle 999.9 ms are available for impedance measurements. A pause of up to 50 ms could be allowed after the square pulse ends in order to allow for relaxation of the tissue in order to avoid disturbance to the impedance measurements. There still remains plenty of time to determine tissue impedance and phase angle data in between the stimulation pulses.

A discrimination algorithm using the phase-angle as function of frequency can facilitate an algorithm less sensitive to variation in the measurement system.

Thus, the new concept is based on a newly discovered mechanism to determine tissue using a specific impedance pattern, as exemplified herein by a pattern for determining when nerve tissue is present. This pattern is obtained by using a needle electrode setup to measure impedance as a function of frequency between 1 Hz and 1 MHz. Known needle electrode setups can be used. Tissue specific differences can be found in a very wide range of frequencies, but measurements have shown that most pronounced differences between the adequate tissue types was found in the range about 1 kHz to 300 kHz.

The typical prior art approach for impedance measurement during peripheral nerve block application has been to measure the impedance modulus level with high energy square pulses (the same pulses used for the stimulation). The high energy precludes the measurement and makes the results very difficult to analyse (The energy have influence on the tissue and its electrical properties. This gives non-linear measurements). Some special arrangements are also required for such setups to extract the necessary frequency components from the square pulse. The pulses must also have well-defined curve shapes.

The measurements for the concept described herein may be done with a 3-electrode setup, using a well-defined multi frequency sinus excitation with low energy. This is done by adding a second skin electrode, and a specially programmed measurement device (se previous application). This gives many other opportunities during the analysis of the measured data.

From different analysis of impedance measured as function of frequency, it has been discovered that information from about 1 kHz to 300 kHz was sufficient to discriminate the nerve tissue from the surrounding tissue types. The key to this is to analyse how the measured impedance parameters varied over the measured frequency range, and not to focus at the level or absolute values at each frequency. In other words: the most important step is not to decide if the impedance parameters (e.g. modulus and phase) are at a certain level (e.g. phase angle=20 or 30 degrees), but to investigate what happens to the parameters as the measurement frequency is increased (e.g. does the phase angle increase or decrease as the measurement frequency is changed from 100 kHz to 200 kHz, and is this change above a certain rate?).

The measured impedance level will vary much between needle types or between single needles due to uneven productions, but the curve shape that we analyses reflects more of the tissue specific properties and is less vulnerable to needle variances that prior art techniques. It is nonetheless preferred to adjust the algorithms for each type of needle for optimal performance.

There are numerous analysing methods that can be used to recognize curve patterns. The key is to know which measurement frequencies to use, and to analyse the variation between frequencies and not only the measured level. Hence, the method used to analyse the data is not very important as long as it can be used to recognize the variation as function of frequency. The invention, at least in the preferred embodiments thereof, is the discovery of a frequency range containing sufficient tissue specific properties, and that at least two measurement frequencies are needed (to point out the change in impedance between frequencies).

The example above used criteria at three different frequencies. This gave high quality discrimination with a small number of measurement frequencies. It would of course be possible to have obtained similar or better results using more than three frequencies. It is also expected to be possible to obtain reasonable results by using only two frequencies.

It will also be appreciated that similar results using the same general principle can be obtained by different techniques to those set out above, for example by using machine learning and other computer/numeric analysis techniques. The advance described herein is based on the realisation that a combination of a threshold for impedance modulus characteristics at one or more selected frequency and a threshold for impedance phase angle characteristics at one or more selected frequency can be used to provide an effective way to discriminate between different tissue types. This applies no matter how the threshold values or frequencies are determined, and hence they may be determined by any suitable technique.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

We claim:

1. A method of determining if a biological tissue region of interest includes intraneural tissue based on a complex impedance spectra that has been obtained from a probe with a conducting part adjacent the tissue region of interest, wherein the impedance spectra includes data from a plurality of frequencies, the method comprising:
   obtaining, from the complex impedance spectra, a first data set representative of impedance modulus values, or equivalent admittance values, at one or more frequencies;
   obtaining, from the complex impedance spectra, a second data set representative of impedance phase angle values, or equivalent admittance values, at one or more different frequencies;

applying a first discrimination criterion to the first data set to determine whether or not the impedance modulus is below a value known to exclude subcutaneous fat tissue;

applying a second discrimination criterion to the second data set to determine if the phase angle at a set frequency is above a threshold level that is known to exclude at least one of muscle tissue and perineural tissue;

applying a third discrimination criterion to the second data set to determine if a gradient of the phase angle at a set frequency is larger than $3/126$ degrees per kHz at a set frequency that is above 10 kHz and below 400 kHz; and thereby determining if the tissue region of interest includes intraneural tissue.

2. A method as claimed in claim 1, comprising obtaining and comparing impedance spectra for known tissue types in order to identify frequencies at which data parameters including two or more of impedance modulus, phase angle, and phase angle gradient have the greatest difference for different tissue types, and selecting discrimination criteria at these frequencies to thereby provide the impedance modulus value for the first discrimination criterion, the threshold phase angle for the second discrimination criterion, and the threshold gradient for the third discrimination criterion.

3. A method as claimed in claim 2, comprising using a compound variable based on the three discrimination criteria to determine if the tissue region of interest includes intraneural tissue.

4. A method as claimed in claim 1, wherein the first discrimination criterion requires an impedance of less than 2500 Ohms at a frequency in the range of 10 kHz to 50 kHz.

5. A method as claimed in claim 1, wherein the first discrimination criterion requires an impedance of less than 2200 Ohms at a frequency of about 39 kHz.

6. A method as claimed in claim 1, wherein the second discrimination criterion requires a phase angle of less than 25 degrees at a frequency selected from the range 10 kHz to 50 KHz.

7. A method as claimed in claim 6, wherein the second discrimination criterion requires a phase angle of less than 25 degrees at about 39 kHz.

8. A method as claimed in claim 1, wherein the third discrimination criterion requires an increase in phase angle of larger than 3 degrees for the phase angle at 251 kHz compared to the phase angle at 125 kHz.

9. A method as claimed in claim 1, wherein the third discrimination criterion excludes phase angle gradients above 0.06 degrees per kHz.

10. A computer programme product comprising instructions that, when executed, will configure a data processing apparatus to carry out the method of claim 1.

11. A method as claimed in claim 1, wherein the third discrimination criterion requires a gradient of larger than $3/126$ degrees per kHz for the phase angle at frequencies above 100 kHz and at frequencies below 300 kHz.

12. A method as claimed in claim 1, further comprising using the impedance modulus, the phase angle and the gradient of the phase angle in order to determine if the tissue region of interest includes vascular tissue or intravascular tissue.

13. An apparatus for determining if a biological tissue region of interest includes intraneural tissue based on a complex impedance spectra that has been obtained from a probe with a conducting part adjacent a tissue region of interest, wherein the impedance spectra includes data from a plurality of frequencies, the apparatus comprising a processor arranged to: obtain, from the complex impedance spectra, a first data set representative of impedance modulus values, or equivalent admittance values, at one or more frequencies; obtain, from the complex impedance spectra, a second data set representative of impedance phase angle values, or equivalent admittance values, at one or more different frequencies; apply a first discrimination criterion to the first data set to determine whether or not the impedance modulus is below a value known to exclude subcutaneous fat tissue; apply a second discrimination criterion to the second data set to determine if the phase angle at a set frequency is above a threshold level that is known to exclude at least one of muscle and perineural tissue; apply a third discrimination criterion to the second data set to determine if a gradient of the phase angle is larger than $3/126$ degrees per kHz at a set frequency that is above 10 kHz and below 400 kHz; and to thereby determine if the tissue region of interest includes intraneural tissue.

14. An apparatus as claimed in claim 13, wherein the processor is arranged to use a compound variable based on the three discrimination criteria to determine if the tissue region of interest includes intraneural tissue.

15. An apparatus as claimed in claim 13, wherein the first discrimination criterion requires an impedance of less than 2500 Ohms at a frequency in the range of 10 kHz to 50 kHz.

16. An apparatus as claimed in claim 13, wherein the second discrimination criterion requires a phase angle of less than 25 degrees at a frequency selected from the range 10 kHz to 50 KHz.

* * * * *